United States Patent [19]
Ikejiri

[11] Patent Number: 5,608,374
[45] Date of Patent: Mar. 4, 1997

[54] HUMIDITY SENSOR AND A METHOD OF PRODUCING THE HUMIDITY SENSOR

[75] Inventor: Masahisa Ikejiri, Suwa, Japan

[73] Assignee: Seiko Epson Corporation, Tokyo, Japan

[21] Appl. No.: 119,165

[22] PCT Filed: Feb. 10, 1993

[86] PCT No.: PCT/JP93/00170

§ 371 Date: Nov. 22, 1993

§ 102(e) Date: Nov. 22, 1993

[87] PCT Pub. No.: WO93/16377

PCT Pub. Date: Aug. 19, 1993

[30] Foreign Application Priority Data

| Feb. 14, 1992 | [JP] | Japan | 4-28251 |
| Mar. 6, 1992 | [JP] | Japan | 4-49903 |
| May 22, 1992 | [JP] | Japan | 4-130290 |
| May 22, 1992 | [JP] | Japan | 4-130291 |
| May 22, 1992 | [JP] | Japan | 4-130292 |

[51] Int. Cl.⁶ ............................................. H01C 7/00
[52] U.S. Cl. ............................................. 338/35; 352/963
[58] Field of Search ............................... 338/35; 252/963

[56] References Cited

U.S. PATENT DOCUMENTS

| 4,041,437 | 8/1977 | Matsuura et al. | 338/35 |
| 4,052,691 | 10/1977 | Nagano et al. | 338/35 |
| 4,210,894 | 7/1980 | Nitta et al. | 338/35 |
| 4,373,391 | 2/1983 | Johnson | 338/35 |
| 4,793,175 | 12/1988 | Fedter et al. | 73/73 |
| 5,136,274 | 8/1992 | Shimomura et al. | 338/35 |
| 5,206,615 | 4/1993 | Fujita et al. | 338/35 |

FOREIGN PATENT DOCUMENTS

| 0013022 | 7/1980 | European Pat. Off. . |
| 0242834 | 10/1987 | European Pat. Off. . |
| 3305683 | 8/1984 | Germany . |
| 49-44295 | 4/1974 | Japan . |
| 52-46495 | 4/1977 | Japan . |
| 57-208101 | 12/1982 | Japan . |
| 58-86447 | 5/1983 | Japan . |
| 61-26162 | 2/1986 | Japan . |
| 61-260601 | 11/1986 | Japan . |
| 63-12757 | 1/1988 | Japan . |
| 63-177050 | 7/1988 | Japan . |
| 63177050 | 7/1988 | Japan . |

*Primary Examiner*—Geoffrey S. Evans
*Assistant Examiner*—Karl Easthom
*Attorney, Agent, or Firm*—Oliff & Berridge

[57] ABSTRACT

A humidity sensor to detect humidity by utilizing a change in the electric characteristics of the device corresponding to a change in the humidity. A solution containing manganese acetate, lead acetate and potassium acetate is coated on an alumina substrate on which interdigital electrodes are formed, and heat-treatment is carried out to provide a humidity sensor having a humidity sensing film which mainly contains manganese oxide, lead oxide and a compound of the alkali metal. The humidity sensor shows a low impedance and an appropriate dynamic range of the impedance even after being downsized. The humidity sensor shows a quick response and excellent environmental resistance. In addition, the humidity sensor and a humidity measuring circuit are easily produced. Thus, the humidity sensor can be widely used in those fields that require a humidity sensor of a small size, a quick response, high reliability and a low cost such as in portable instruments and the like.

22 Claims, 12 Drawing Sheets

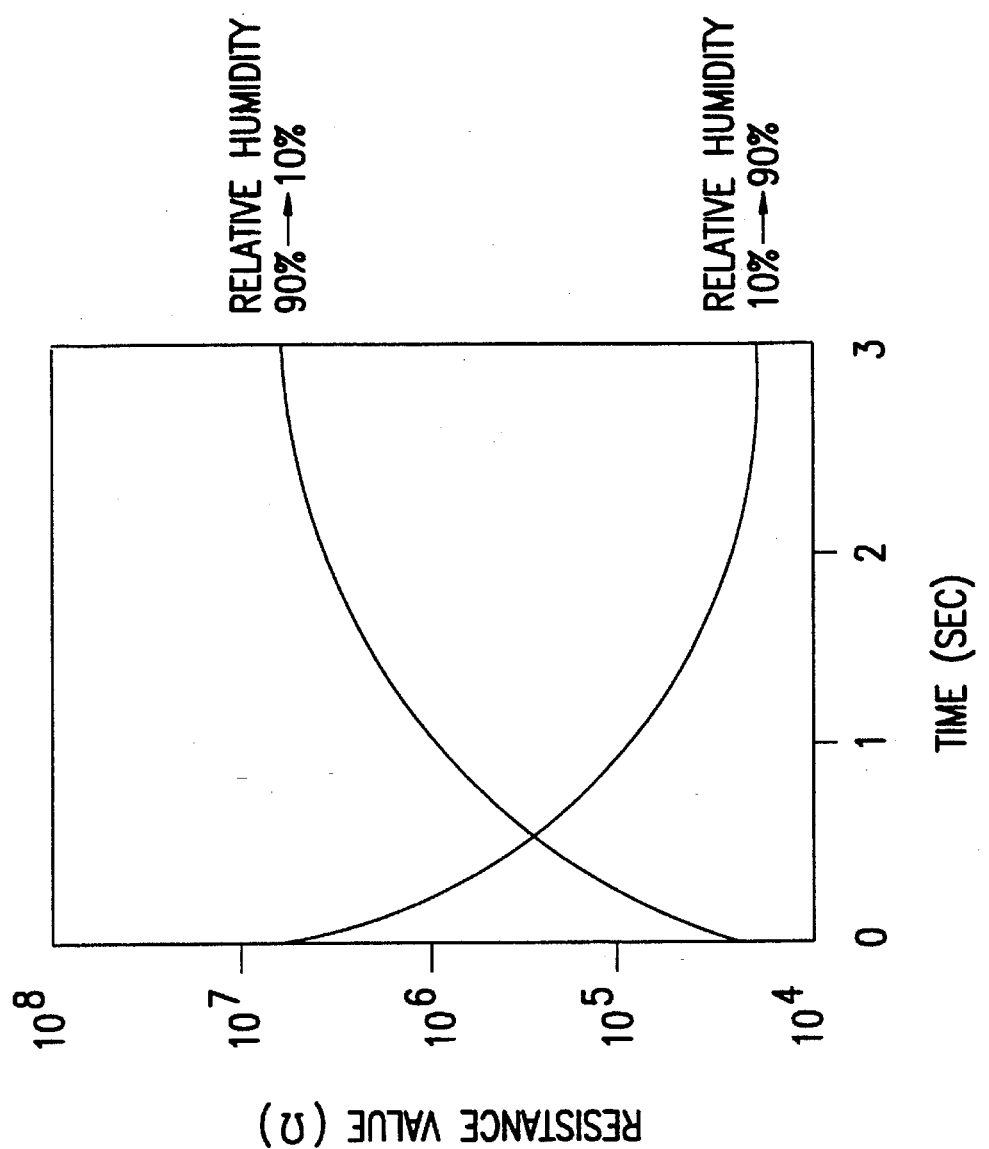

HUMIDITY SENSOR AND A METHOD OF PRODUCING THE HUMIDITY SENSOR

TECHNICAL FIELD

This invention relates to a humidity sensor which detects humidity by utilizing a change in electric characteristics of the device corresponding to a change in the humidity.

BACKGROUND ART

Along with the recent increase in number of the fields where measurement and control of humidity is required, the importance of the humidity sensor has been appreciated.

The humidity sensor which detects humidity by utilizing a change in electric characteristics of the device corresponding to a change in the humidity includes those of an electrolyte type, a metal type, a polymer type and a ceramics type, and various materials have been investigated in each type, however, at moment, humidity sensors of a polymer type and a ceramics type have been practically used. Both types of the sensors utilize their property that the impedance or the electric capacity of the device is changed by absorption and desorption of the water onto the device.

However, the prior art humidity sensors have some problems in their downsizing. When the prior art technique is employed for producing a humidity sensor of a small size, the impedance is raised and the fluctuation of the impedance from one device to another is increased. Besides, the dynamic range of the impedance becomes too big or too small. Accordingly, it has been difficult to produce a small hydrometer of high precision.

Many of the prior art humidity sensors have a slow response, thus it has been impossible to measure the humidity change correctly.

From the view point of the reliability, the prior art humidity sensors are not resistant to a high temperature, high humidity or an organic solvent, and when they are immersed in water, many of them are deteriorated. Furthermore, when they are contacted with an electrolyte solution such as a salt water, even after being dried, the electrolyte remains in the humidity sensing body, and the characteristics are very much changed to make the device unusable. With an organic solvent, as the humidity sensing body is dissolved in it, the characteristics are very much changed and the device becomes unusable.

The present invention is to solve these problems, and its object is to provide a humidity sensor having, in addition to a quick response and high environmental resistance, a low impedance and an appropriate dynamic range of the impedance even after the sensor is downsized.

DISCLOSURE OF THE INVENTION

According to one aspect of the present invention, there is provided a humidity sensor employing a humidity sensing body containing manganese oxide, lead oxide and an alkali metal compound as the main components.

According to another aspect of the present invention, there is provided a humidity sensor employing a humidity sensing body containing manganese oxide and an alkali metal compound as the main components.

According to still another aspect of the present invention, there is provided a humidity sensor employing a humidity sensing body containing lead oxide and an alkali metal compound as the main components.

By the use of the humidity sensing body having such components, a humidity sensor which has a low impedance and an appropriate dynamic range of the impedance, can be obtained even when the sensor is downsized.

By forming the humidity sensing body in the form of a film on a substrate, a humidity sensor having a small size and a quick response can be produced in a simple process with a low cost. In this description, the humidity sensing body formed in the form of the film is referred to as a humidity sensing film.

Manganese oxide does not need to be manganese oxide as the starting material, and those which can provide manganese oxide by decomposition, such as manganese carbonate, manganese acetate and manganese nitrate can be used as well. Similarly, lead oxide does not need to be lead oxide as the starting material, and those which can provide lead oxide by decomposition, such as lead carbonate, lead acetate and lead nitrate can be used as well. Manganese oxide, lead oxide and a compound of the alkali metal do not need to be heat-treated simultaneously; in one illustrative process, a substrate may be immersed firstly in a solution of lead acetate, followed by heat-treatment, then immersed in a solution of manganese nitrate, followed by heat-treatment, and immersed in a solution of sodium carbonate and followed by heat-treatment.

When a fluorine-contained polymer film is formed to cover the humidity sensing body, a humidity sensor of very high reliability whose characteristics do not change even when it is immersed in an electrolyte solution or an organic solvent can be provided.

For mounting the humidity sensor on an instrument of waterproof structure, an O-ring is sometimes used for waterproofing purpose. In such a case, an advantageous application for a small or a water proof instrument may be forming interdigital electrodes of a circular form on a substrate, and forming a humidity sensing film on the electrodes, since it can provide a good space factor.

Referring now to small size instruments, when electrodes and the humidity sensing film are formed on the substrate, it is advantageous to provide terminal parts on an opposite surface of the substrate from the surface on which the humidity sensing film is provided, since it improves the space factor. In such a case, the electrodes on the side of the humidity sensing film can be electrically connected to terminals provided on the side opposite from the humidity sensing film via through-holes provided on the substrate or via the side surfaces of the substrate.

As a substrate, an alumina substrate, a glass substrate or a silicon substrate is desirable from the view point of reliability and mass productivity. A silicon substrate on which an insulating film is formed by heat-oxidation, sputtering or CVD and the like, can be used as an insulating substrate.

As an electrode, a metal selected from Au, Ag, Pt and Pd, or an alloy containing at least one of these elements is desirable from the view point of reliability, and an interdigital electrode is advantageously employed for decreasing the impedance.

According to yet another aspect of the present invention, a method of producing a humidity sensor comprises forming a humidity sensing film by coating a solution containing manganese ion, lead ion and an alkali metal ion on a substrate and by carrying out heat-treatment.

According to yet another aspect of the present invention, a method of producing a humidity sensor comprises forming a humidity sensing film by coating a solution containing manganese ion and an alkali metal ion on a substrate and by carrying out heat-treatment.

According to yet another aspect of the present invention, a method of producing a humidity sensor comprises forming a humidity sensing film by coating a solution containing lead ion and an alkali metal ion on a substrate and by carrying out heat-treatment.

Referring now to forming the humidity sensing body in the form of a film, the humidity sensing film can be produced by dissolving a salt such as a nitrate or an acetate in a solvent, coating the solution on a substrate, then carrying out heat-treatment. Thus the humidity sensor can be easily produced with a low cost. As a means of coating, many processes such as screen printing, spin coating, dip coating and roll coating can be used. As the coating liquid, a solution of an alkoxide can be used in addition to the above mentioned salt solutions. According to this production method, the control of composition, the control of micro structure, and the control of porosity can be easily done and a humidity sensor of higher quality can be obtained.

BRIEF DESCRIPTION OF THE DRAWINGS

FIG. 23 illustrates response characteristics of a humidity sensor of the present invention.

EXPLANATION OF THE REFERENCE NUMERALS

Numeral 1 designates a humidity sensing body or a humidity sensing film.

Numeral 2 designates an electrode.

Numeral 3 designates a lead wire.

Numeral 4 designates a substrate.

Numeral 5 designates a fluorine contained polymer film.

Numeral 6 designates an O-ring.

Numeral 7 designates a main body of a small size waterproof instrument.

Numeral 8 designates a through-hole.

Numeral 9 designates a terminal part.

Numeral 10 designates a conducting part.

Numeral 11 designates an insulating film.

The Best Mode for Carrying Out the Invention

The present invention will be explained in detail according to the accompanying drawings.
Embodiment 1

Figure 1:
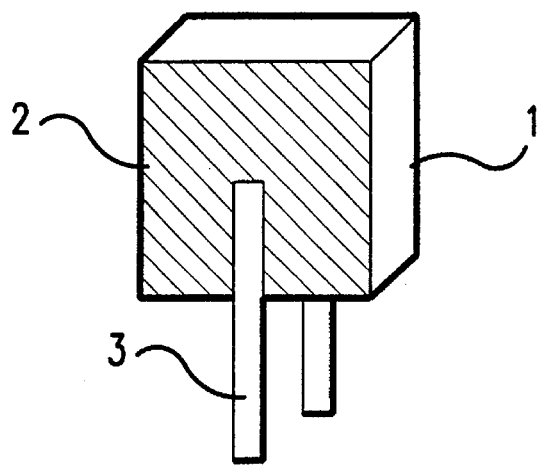
FIG. 1 is a perspective view of a humidity sensor of the present invention.
Figure 2:
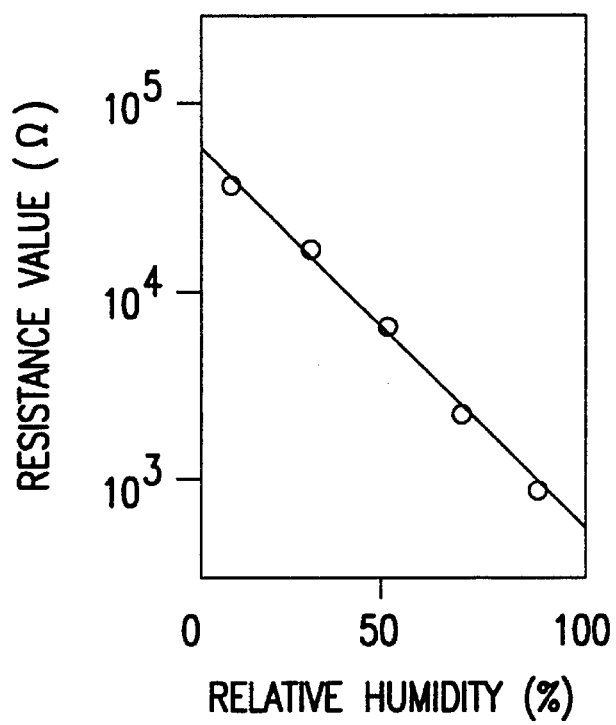
FIG. 2 illustrates humidity sensing characteristics of a humidity sensor of the present invention.

20 g of manganese dioxide, 20 g of lead oxide and 10 g of lithium carbonate were mixed, molded by pressing followed by heat-treatment at 600° C. for one hour to form a humidity sensing body mainly containing manganese oxide, lead oxide and a compound of the alkali metal. A cube of 5 mm×5 mm×5 mm was cut out from the obtained humidity sensing body, Ag electrodes were attached to it to form such a humidity sensor that is shown in FIG. 1. Referring to FIG. 1, the reference numeral 1 designates the humidity sensing body, the reference numeral 2 designates the electrode and the reference numeral 3 designates a lead wire. The humidity sensing characteristics of this humidity sensor are shown in FIG. 2. From the FIG. 2, it is found out that the humidity sensor of the present invention is easy to use, since it has a low impedance, and the dynamic range of the impedance is appropriate.
Embodiment 2

100 ml of ethanol, 80 g of manganese acetate, 20 g of lead acetate and 10 g of potassium acetate were added to 100 ml of water and stirred for one hour. The resulting solution was coated by dip coating on an alumina substrate on which interdigital electrodes were formed by screen printing of an Au paste and heat-treatment at 500° C. was carried out for one hour to produce a humidity sensing film mainly containing manganese oxide, lead oxide and a compound of the alkali metal.

Figure 3:
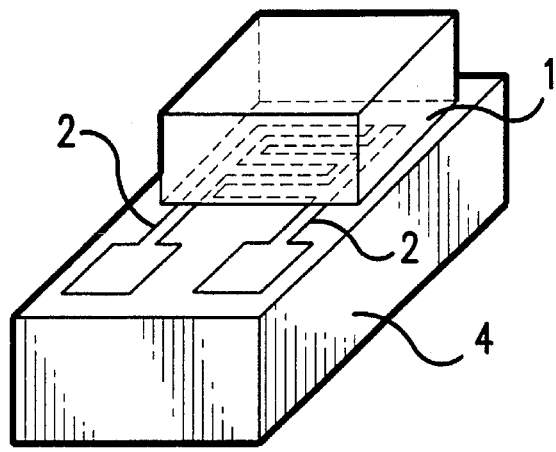
FIG. 3 is a perspective view of a humidity sensor of the present invention.
Figure 4:
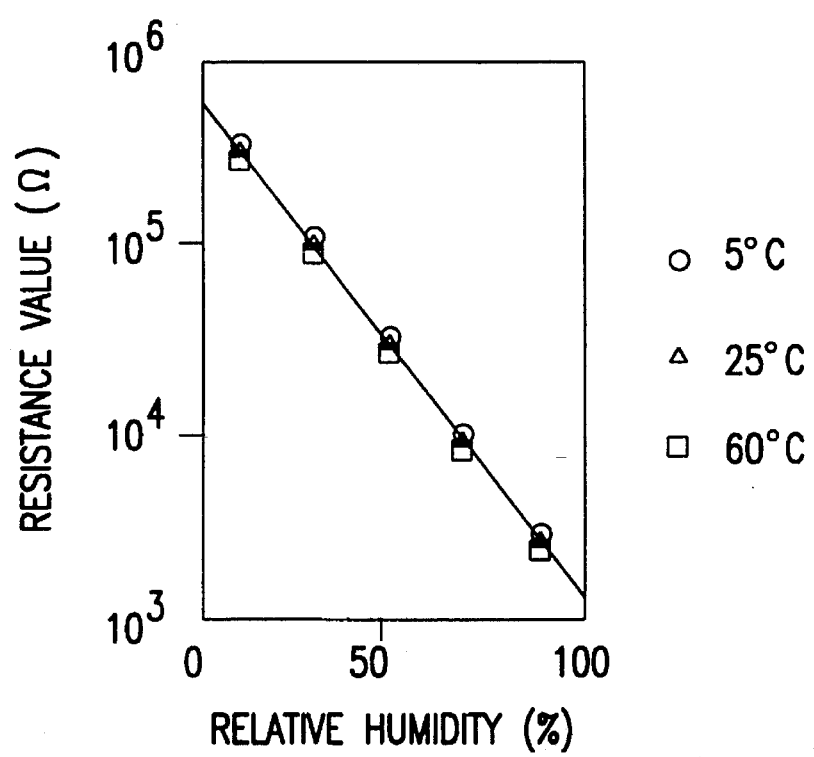
FIG. 4 illustrates humidity sensing characteristics of-a humidity sensor of the present invention.

A perspective view of the humidity sensor thus produced is shown in FIG. 3. Referring to FIG. 3, the reference numeral 1 designates the humidity sensing film, the reference numeral 2 designates the electrode and the reference numeral 4 designates the substrate. The humidity sensing characteristics of this humidity sensor are shown in FIG. 4. From the FIG. 4 it is found out that the humidity sensor of the present invention is easy to use since it has a low impedance, the dynamic range of the impedance is appropriate and the characteristics do not change according to the temperature. The characteristics of the humidity sensor measured after the sensor had been kept in a thermo-hygrostat of 60° C. and 90% for 1000 hours, were similar to those shown in FIG. 4 within the limit of error of the measurement. Accordingly, it is clear that the present humidity sensor has high durability and high reliability.

Embodiment 3

Figure 5:
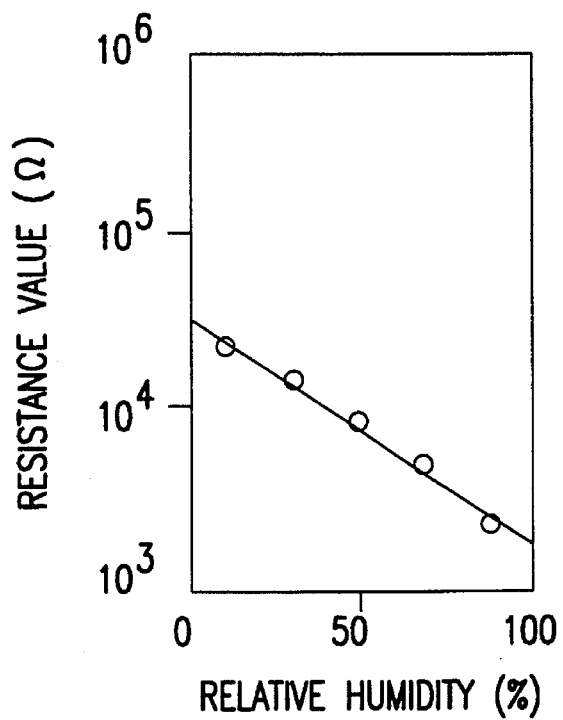
FIG. 5 illustrates humidity sensing characteristics of a humidity sensor of the present invention.

100 ml of glycerin, 40 g of lead acetate and 30 g of sodium acetate were added to 100 ml of water and stirred for one hour. The solution was coated by spin coating on a glass substrate on which interdigital electrodes were formed by deposition of Cr and Au in this order, and heat-treatment was carried out at 400° C. for one hour. The substrate was immersed in a solution of manganese nitrate (72 wt %), then heat-treatment at 200° C. was carried out for one hour. A perspective view of the humidity sensor thus prepared is shown in FIG. 3, and the humidity sensing characteristics of the humidity sensor are shown in FIG. 5.

Embodiment 4

Figure 6:
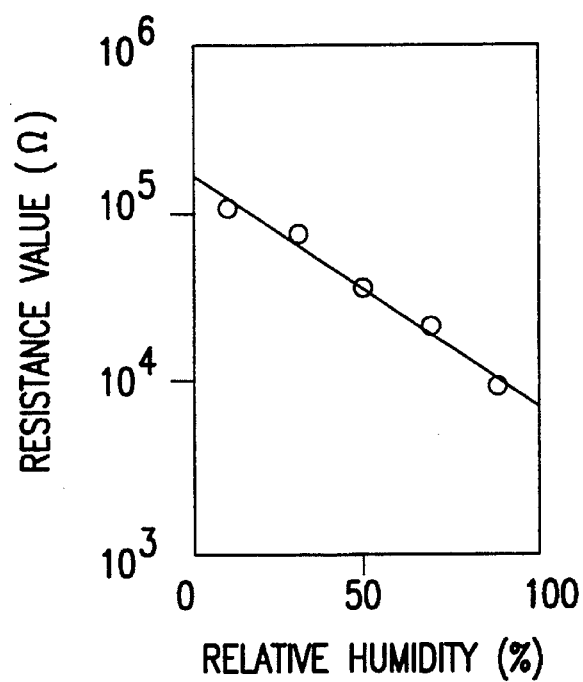
FIG. 6 illustrates humidity sensing characteristics of a humidity sensor of the present invention.

A lead nitrate solution (40 wt %) was coated by roll coating on a quartz glass substrate on which Pt-Pd interdigital electrodes were formed by screen printing, and heat-treated at 700° C. for one hour. Then the substrate was immersed in a solution of manganese nitrate (50 wt %), and heat-treated at 300° C. for one hour. The substrate was then immersed in a solution of sodium nitrate (60 wt %) and then heat-treated at 500° C. for one hour. A perspective view of the humidity sensor thus prepared is shown in FIG. 3, and the humidity sensing characteristics of the humidity sensor are shown in FIG. 6.

Embodiment 5

Figure 7:
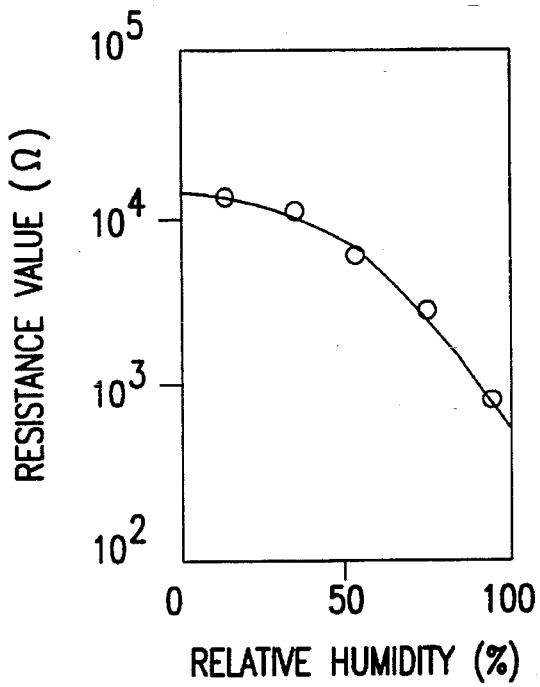
FIG. 7 illustrates humidity sensing characteristics of a humidity sensor of the present invention.

20 g of manganese dioxide is mixed with 10 g of lithium carbonate, molded by pressing, followed by heat-treatment at 600° C. for one hour to prepare a humidity sensing body mainly containing manganese oxide and a compound of the alkali metal. A cube of 5 mm×5 mm×5 mm was cut out from the obtained humidity sensing body, $RuO_2$ electrodes were attached to it to form such a humidity sensor that is shown in FIG. 1. The humidity sensing characteristics of this humidity sensor are shown in FIG. 7.

Embodiment 6

100 ml of ethanol, 80 g of manganese acetate and 10 g of potassium acetate were added to 100 ml of water and stirred for one hour. The resulting solution was coated by dip coating on an alumina substrate on which interdigital electrodes were formed by screen printing of an Au paste and heat-treatment at 500° C. was carried out for one hour to produce a humidity sensing film mainly containing manganese oxide and a compound of the alkali metal.

Figure 8:
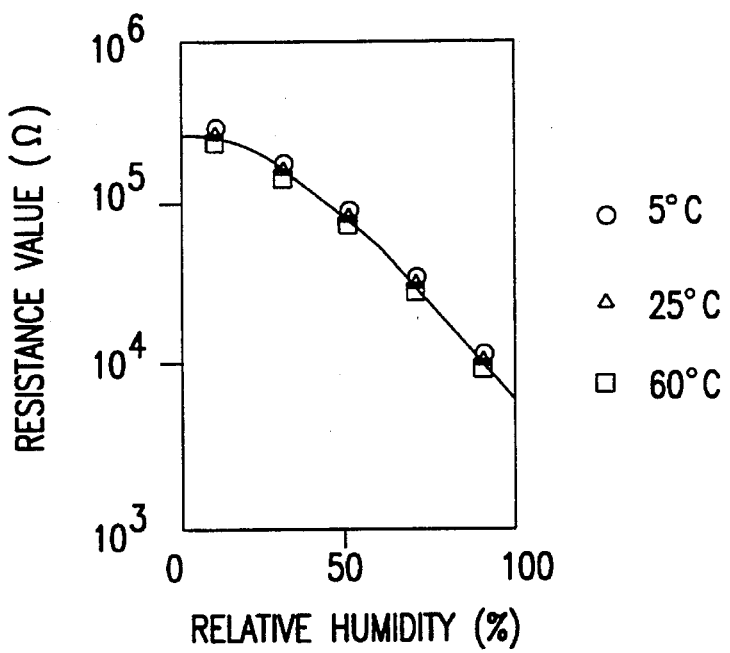
FIG. 8 illustrates humidity sensing characteristics of a humidity sensor of the present invention.

A perspective view of the humidity sensor thus produced is shown in FIG. 3, and the humidity sensing characteristics of the humidity sensor are shown in FIG. 8. The characteristics of the humidity sensor measured after the sensor had been kept in a thermo-hygrostat of 60° C. and 90% for 1000 hours, were similar to those shown in FIG. 8 within the limit of error of the measurement. Accordingly, it is clear that the present humidity sensor has high durability and high reliability.

Embodiment 7

Figure 9:
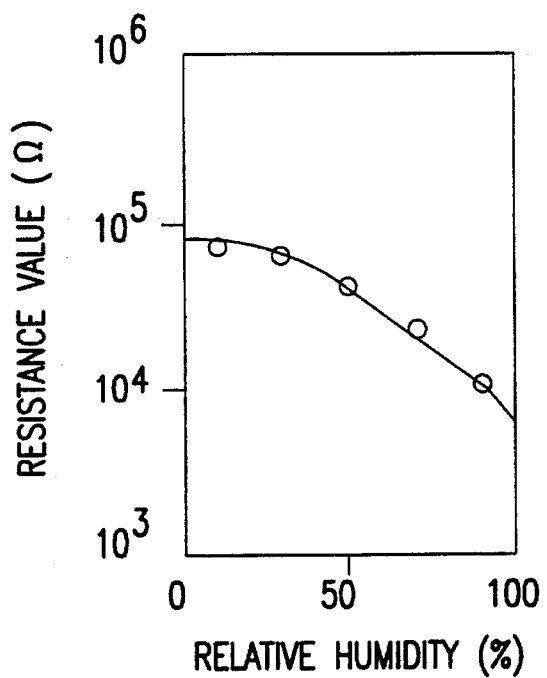
FIG. 9 illustrates humidity sensing characteristics of a humidity sensor of the present invention.

100 ml of glycerin and 100 g of manganese nitrate were added to 100 ml of water and stirred for one hour. The solution was coated by spin coating on a glass substrate on which interdigital electrodes were formed by deposition of Cr and Au in this order, and heat-treatment was carried out at 400° C. for one hour. The substrate was immersed in a solution of sodium nitrate (50 wt %), then heat-treatment at 200° C. was carried out for one hour. A perspective view of the humidity sensor thus prepared is shown in FIG. 3, and the humidity sensing characteristics of the humidity sensor are shown in FIG. 9.

Embodiment 8

Figure 10:
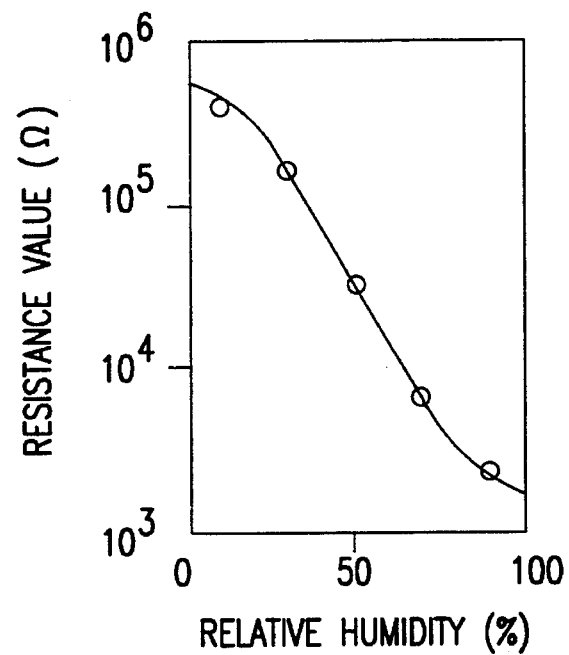
FIG. 10 illustrates humidity sensing characteristics of a humidity sensor of the present invention.

A manganese nitrate solution (72 wt %) was coated by roll coating on a quartz glass substrate on which Pt—Pd interdigital electrodes were formed by screen printing and heat-treatment was carried out at 700° C. for one hour. Then the substrate was immersed in a solution of lithium chloride (60 wt %), and heat-treated at 500° C. for one hour. A perspective view of the humidity sensor thus prepared is shown in FIG. 3, and the humidity sensing characteristics of the humidity sensor are shown in FIG. 10.

Embodiment 9

Figure 11:
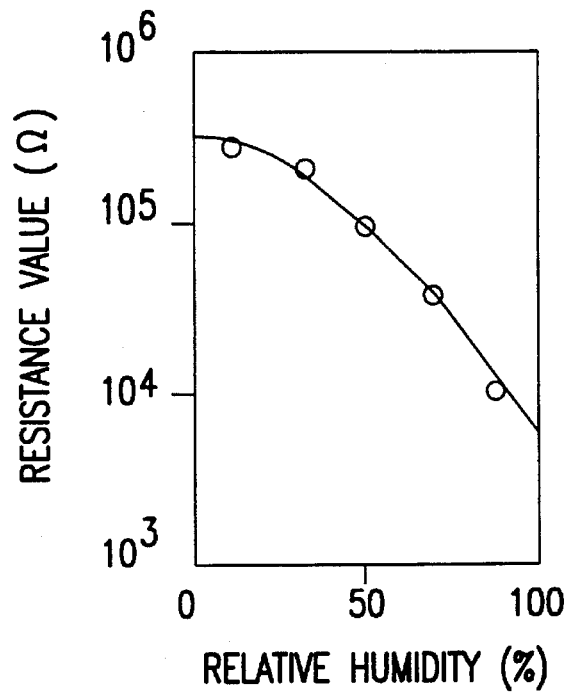
FIG. 11 illustrates humidity sensing characteristics of a humidity sensor of the present invention.

20 g of lead oxide was mixed with 10 g of lithium carbonate, and molded by pressing, followed by heat-treatment at 600° C. for one hour to prepare a humidity sensing body mainly containing lead oxide and a compound of the alkali metal. A cube of 5 mm×5 mm×5 mm was cut out from the obtained humidity sensing body, Ag—Pd electrodes were attached to it to form such a humidity sensor that is shown in FIG. 1. The humidity sensing characteristics of this humidity sensor are shown in FIG. 11.

Embodiment 10

100 ml of ethanol, 40 g of lead acetate and 10 g of potassium acetate were added to 100 ml of water and stirred for one hour. The resulting solution was coated by dip coating on an alumina substrate on which interdigital electrodes are formed by screen printing of an Au paste and heat-treatment at 500° C. was carried out for one hour to produce a humidity sensing film mainly containing lead oxide and a compound of the alkali metal.

Figure 12:
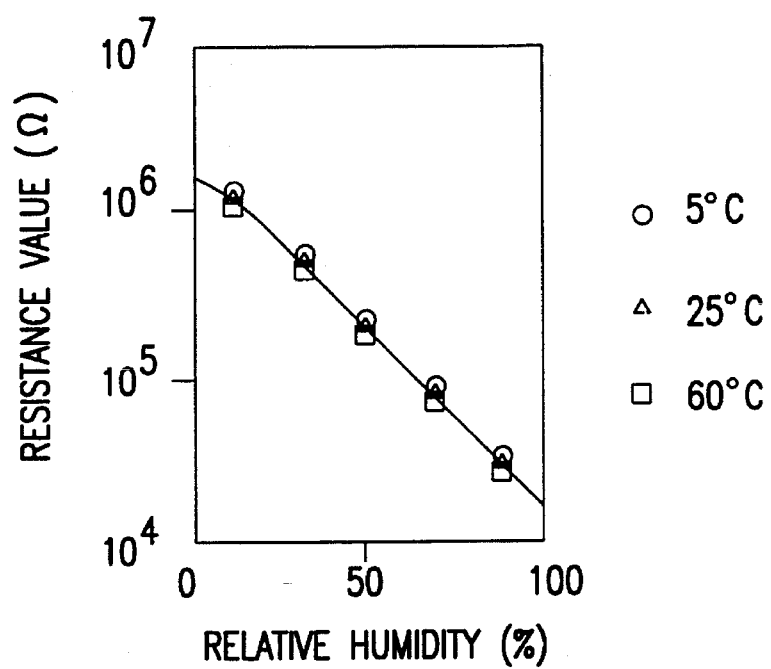
FIG. 12 illustrates humidity sensing characteristics of a humidity sensor of the present invention.

A perspective view of the humidity sensor thus produced is shown in FIG. 3, and the humidity sensing characteristics of the humidity sensor are shown in FIG. 12. The characteristics of the humidity sensor measured after the sensor had been kept in a thermo-hygrostat of 60° C. and 90% for 1000 hours, were Similar to those shown in FIG. 12 within the limit of error of the measurement. Accordingly, it is clear that the present humidity sensor has high durability and high reliability.

Embodiment 11

Figure 13:
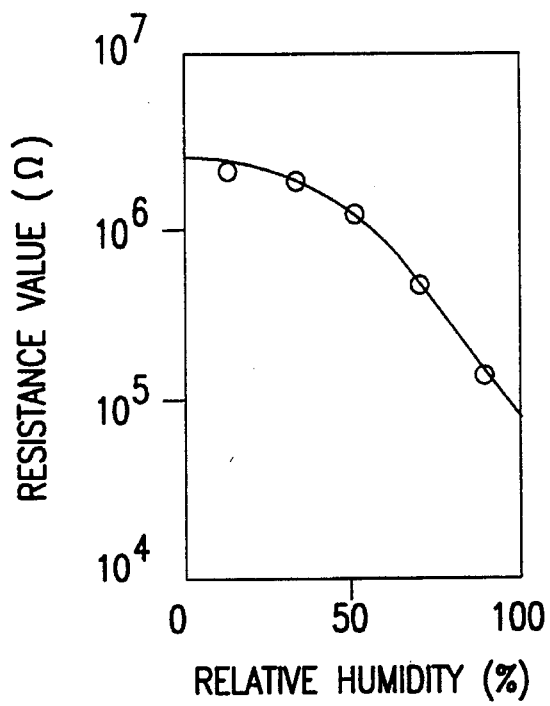
FIG. 13 illustrates humidity sensing characteristics of a humidity sensor of the present invention.

100 ml of glycerin and 40 g of lead nitrate were added to 100 ml of water and stirred for one hour. The solution was coated by spin coating on a glass substrate on which interdigital electrodes were formed by deposition of Cr and Au in this order and heat-treatment was carried out at 400° C. for one hour. The substrate was immersed in a solution of sodium nitrate (50 wt %), then heat-treatment at 200° C. was carried out for one hour. A perspective view of the humidity sensor thus prepared is shown in FIG. 3, and the humidity sensing characteristics of the humidity sensor are shown in FIG. 13.

Embodiment 12

Figure 14:
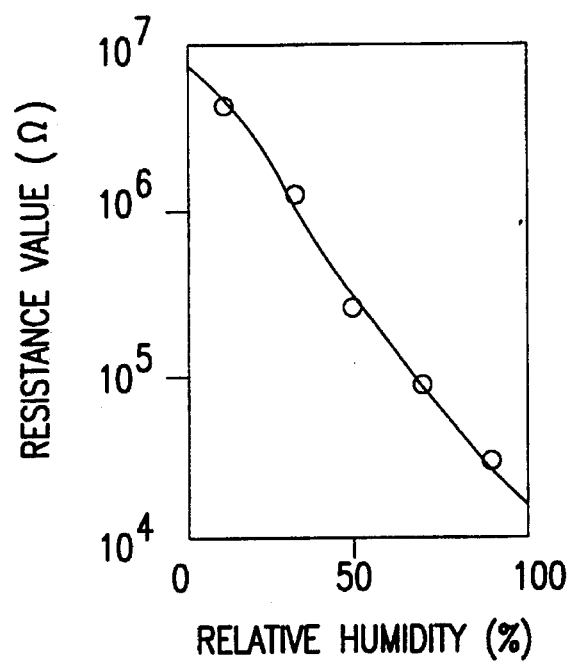
FIG. 14 illustrates humidity sensing characteristics of a humidity sensor of the present invention.

A lead nitrate solution (20 wt %) was coated by roll coating on a quartz glass substrate on which Pt—Pd interdigital electrodes were formed by screen printing, and heat-treated at 700° C. for one hour. Then the substrate was immersed in a solution of lithium chloride (60 wt %), and heat-treated at 500° C. for one hour. A perspective view of the humidity sensor thus prepared is shown in FIG. 3, and the humidity sensing characteristics of the humidity sensor are shown in FIG. 14.

Embodiment 13

50 ml of ethanol, 10 g of manganese acetate, 50 g of lead acetate and 20 g of potassium acetate were added to 100 ml of water and stirred for one hour. The resulting solution was coated by screen printing on an alumina substrate on which interdigital electrodes were formed by screen printing of a Pt paste and heat-treatment at 700° C. was carried out for 20 hours to produce a humidity sensing film mainly containing manganese oxide, lead oxide and a compound of the alkali metal. Here, the size of the humidity sensing part was 1 mm×1 mm. A 10 wt % solution of a solvent-soluble fluorine contained-polymer in perfluoro solvent was coated on the humidity sensing film by screen printing, then heat-treatment was carried out at 180° C. for one hour to form a fluorine contained polymer film.

Figure 15:
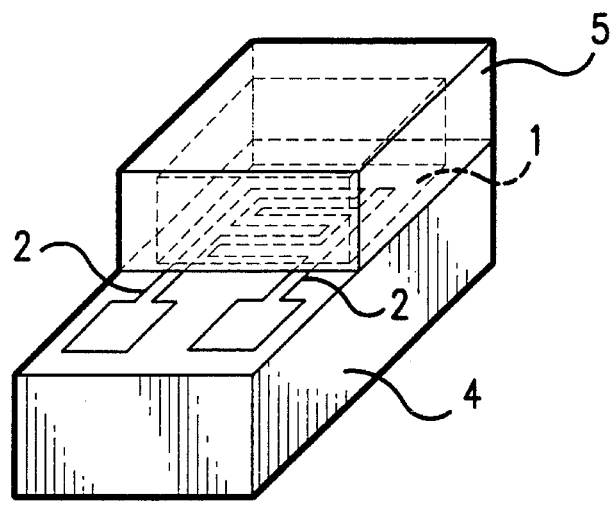
FIG. 15 is a perspective view of a humidity sensor of the present invention.
Figure 16:
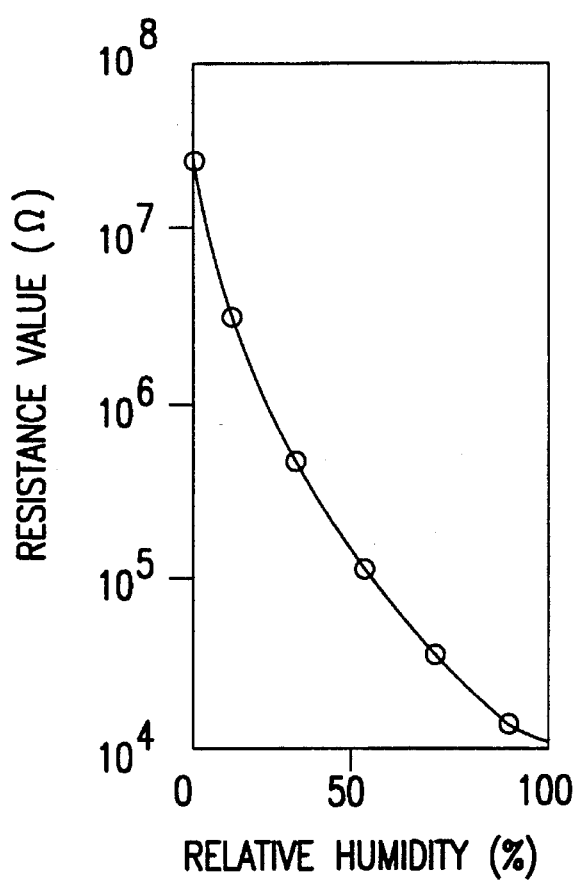
FIG. 16 illustrates humidity sensing characteristics of a humidity sensor of the present invention.

A perspective view of the humidity sensor thus produced is shown in FIG. 15. Referring to. FIG. 15, the reference numeral 1 designates the humidity sensing film, the reference numeral 2 designates the electrode, the reference numeral 4 designates the substrate and the reference numeral 5 designates the fluorine contained polymer film. The humidity sensing characteristics of this humidity sensor are shown in FIG. 16. The present humidity sensor has a low impedance and the dynamic range of the impedance is appropriate though the size of the humidity sensing part is very small.

The characteristics of this humidity sensor measured after the sensor had been immersed in a saturated sodium chloride solution at 60° C. for 100 hours, were similar to those shown in FIG. 16 within the limit of error of the measurement. The characteristics of the humidity sensor measured-after the sensor had been immersed in ethanol at 60° C. for 100 hours, were also similar to those shown in FIG. 16 within the limit of error of the measurement. Accordingly, it is clear that the present humidity sensor has high environmental resistance and high reliability.

Embodiment 14

Figure 17:
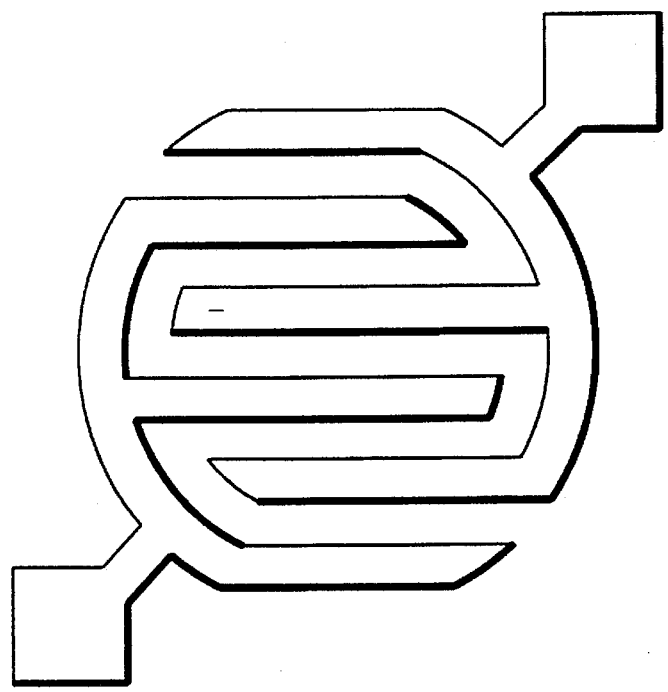
FIG. 17 illustrates an electrode pattern of a humidity sensor of the present invention.

Circular interdigital electrodes (having a diameter of 1 mm) shown in FIG. 17 were formed by Au plating on an alumina substrate. 50 ml of ethanol, 20 g of manganese acetate, 10 g of lead acetate and 50 g of potassium acetate were added to 100 ml of water, stirred for one hour to form a coating liquid for a humidity sensing film. This humidity sensing film use coating liquid was coated by spray coating on the alumina substrate on which the circular interdigital electrodes were formed, and heat-treated at 800° C. for one hour.

Figure 18:
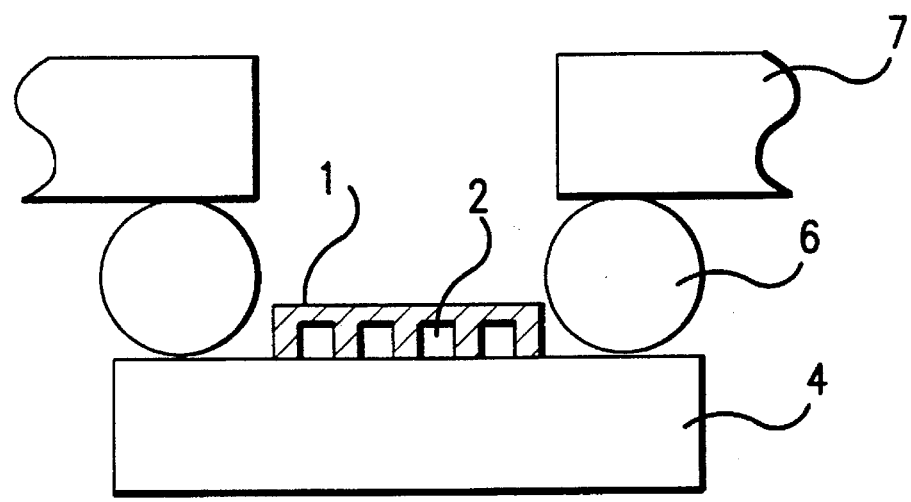
FIG. 18 is a sectional view of an example wherein a humidity sensor of the present invention is mounted.

A sectional view of one example wherein the humidity sensor thus produced was mounted on a small waterproof instrument is shown in FIG. 18. Referring to FIG. 18, the reference numeral 1 designates the humidity sensing film, the reference numeral 2 designates the electrode, the reference numeral 4 designates the substrate, the reference numeral 6 designates an O-ring and the reference numeral 7 designates a main body of the small waterproof instrument. Accordingly, it is clear that the present humidity sensor has a good space factor when it is mounted on a small instrument or a waterproof instrument and contributes to the downsizing of the instrument.

Embodiment 15

Interdigital electrodes were formed on one side of an alumina substrate and terminal parts were formed on the opposite side by screen printing of an Au—Pd paste. The interdigital electrodes and the terminal parts were connected by the Au—Pd paste utilizing through-holes provided on the alumina substrate. The humidity sensing film use coating liquid used in the Embodiment 14 was coated by spin coating on the surface where the interdigital electrodes were formed, and heat-treated at 700° C. for 10 hours.

Figure 19:
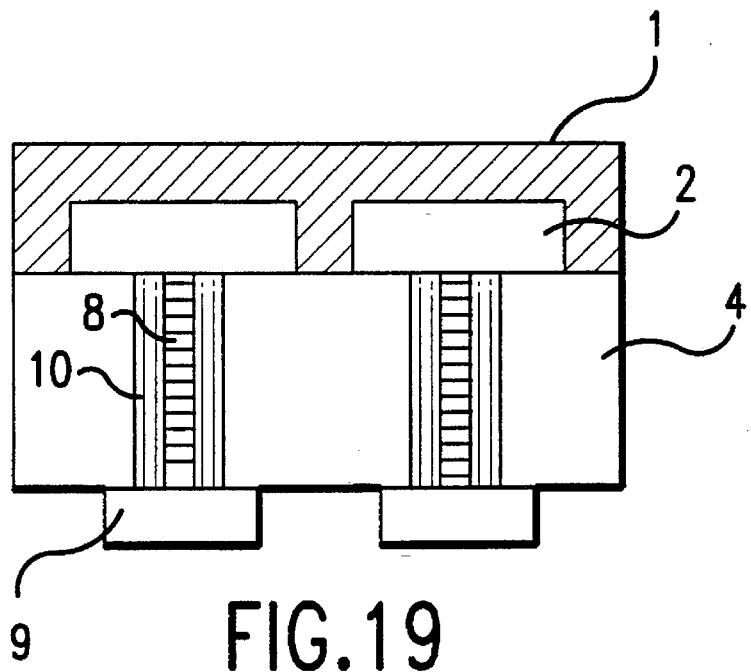
FIG. 19 is a sectional view of a humidity sensor of the present invention.

A sectional view of the humidity sensor thus prepared is shown in FIG. 19. Referring to FIG. 19, the reference numeral 1 designates the humidity sensing film, the reference numeral 2 designates the electrode, the reference numeral 4 designates the substrate, the reference numeral 8 designates the through-holes, the reference numeral 9 designates the terminal parts and the reference numeral 10 designates the conducting parts utilizing the through-holes. Accordingly, the present humidity sensor has a good space factor when it is mounted on a small instrument and contributes to the downsizing of the instrument. Also in the production process, a treatment to prevent the humidity sensing film from being formed on the terminal parts can be eliminated, and the cost is lowered.

Embodiment 16

Interdigital electrodes were formed on one side a glass substrate and terminal parts were formed on the opposite side by screen printing of an Ag—Pd paste. The interdigital electrodes and the terminal parts were connected by the Ag—Pd paste by utilizing the side surfaces of the glass substrate. The humidity sensing film use coating liquid used in the Embodiment 14 was coated by roll coating on the surface where the interdigital electrodes were formed, and heat-treated at 600° C. for 10 hours.

Figure 20:
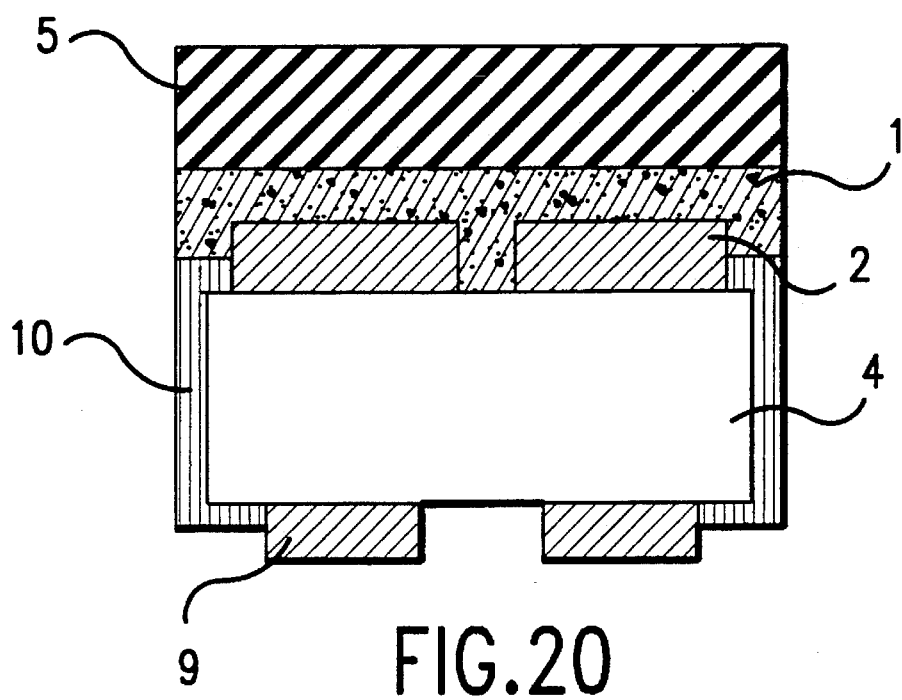
FIG. 20 is a sectional view of a humidity sensor of the present invention.

A sectional view of the humidity sensor thus prepared is shown in FIG. 20. Referring to FIG. 20, the reference numeral 1 designates the humidity sensing film, the reference numeral 2 designates the electrode, the reference numeral 4 designates the substrate, the reference numeral 9 designates the terminal part and the reference numeral 10 designates the conducting part utilizing the side surface.

Embodiment 17

A silicon substrate was heat-treated at 1100° C. for four hours to oxidize the surface to form $SiO_2$ insulating film. Cr and Au were sputtered on the silicon substrate in this order and etched to produce interdigital electrodes. The size of the humidity sensing part was 0.5 mm×0.5 mm. The humidity sensing film use coating liquid used in the Embodiment 14 was coated on the silicon substrate by spin coating and heat-treated at 700° C. for one hour to form a humidity sensing film mainly containing manganese oxide, lead oxide and a compound of the alkali metal. A 1 wt % solution of a solvent-soluble fluorine contained polymer in perfluoro solvent was coated on it by spin coating and heat-treated at 80° C. for one hour to form a fluorine contained polymer film.

Figure 21:
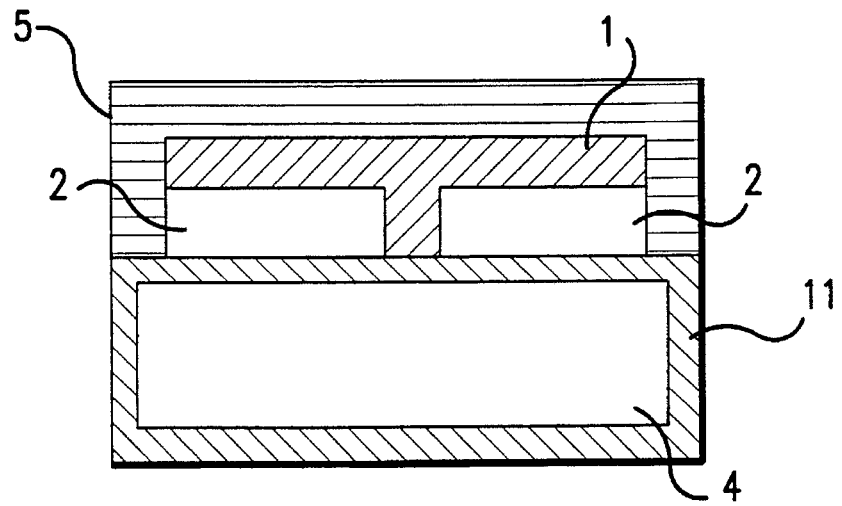
FIG. 21 is a sectional view of a humidity sensor of the present invention.
Figure 22:
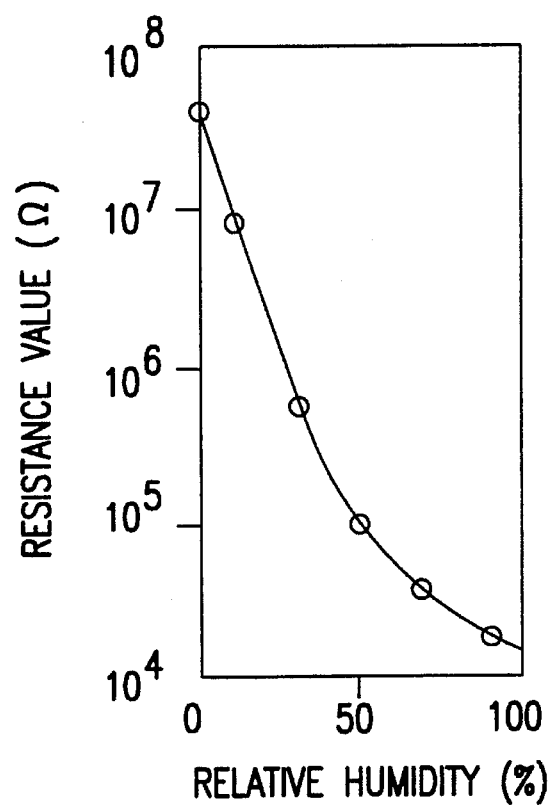
FIG. 22 illustrates humidity sensing characteristics of a humidity sensor of the present invention.

A sectional view of-the humidity sensor thus prepared is shown in FIG. 21. Referring to FIG. 21, the reference numeral 1 designates the humidity sensing film, the reference numeral 2 designates the electrode, the reference numeral 4 designates the substrate, the reference numeral 5 designates the fluorine contained polymer film and the reference numeral 11 designates the insulating film. The humidity sensing characteristics of this humidity sensor are shown in FIG. 22. This humidity sensor has a low impedance and an appropriate dynamic range of the impedance, though the size of the humidity sensing part is very small. The response to the temperature change of within 3 seconds, and the response to the humidity change of within 2 seconds as shown in FIG. 23, are found to be quick enough.

The characteristics of this humidity sensor measured after the sensor had been immersed in acetone for 100 hours, were similar to those shown in FIG. 22 within the limit of error of the measurement. The characteristics of the humidity sensor measured after the sensor had been left in a vessel filled with cigarette smoke for 100 hours were similar to those shown in FIG. 22 within the limit of error of the measurement. Accordingly, it is clear that the present humidity sensor has high environmental resistance and high reliability.

As described above, the humidity sensor of the present invention shows a low impedance and the dynamic range of the impedance is appropriate even after being downsized. Accordingly, a humidity sensor of a small size can be easily produced and the humidity measurement circuit can be readily produced. Thus, the humidity sensing devices can be produced with a low cost. The sensor shows a quick response and good environmental resistance as well. When a fluorine contained polymer film is formed to cover the humidity sensing part, the humidity sensor of very high reliability, whose characteristics will not be changed even when it is immersed in an electrolyte solution or in an organic solvent, can be obtained.

Industrial Applicability

As described above, the humidity sensor of the present invention can be widely applied in fields where measurement and control of humidity is necessary, especially in those fields requiring a humidity sensor of a small size, a quick response, high reliability and a low cost, or in portable instruments and the like.

I claim:

1. A humidity sensor, comprising:
    a humidity sensing film on a first surface of a substrate, the humidity sensing film comprised of an alkali metal compound and a metal oxide selected from the group consisting of manganese oxide, lead oxide and mixtures thereof;
    at least two electrodes upon the first surface of the substrate and covered by the humidity sensing film;
    a fluorine polymer film coating the humidity sensing film; and
    terminal parts formed on a second surface of the substrate, wherein one of the terminal parts is electrically coupled to one of the at least two electrodes.

2. The humidity sensor according to claim 1, wherein the humidity sensing film is formed mainly of said alkali metal compound and said mixture of manganese oxide and lead oxide.

3. The humidity sensor according to claim 2, wherein the humidity sensing film comprises approximately 0.0 to 85.5 weight percent of manganese oxide, approximately 0.0 to 83.0 weight percent of lead oxide and approximately 10.7 to 64.9 weight percent of alkali metal compound.

4. The humidity sensor according to claim 1, wherein the humidity sensing film is formed mainly of said manganese oxide and said alkali metal compound.

5. The humidity sensor according to claim 1, wherein the humidity sensing body is formed mainly of lead oxide and an alkali metal compound.

6. The humidity sensor according to claim 1, wherein the at least two electrodes comprise circular interdigital electrodes.

7. The humidity sensor according to claim 6, wherein the circular interdigital electrodes are made of a metal selected from a group consisting of Au, Ag, Pt and Pd or an alloy containing at least one element selected from the group consisting of Au, Ag, Pt and Pd.

8. The humidity sensor according to claim 1, wherein the first surface of the substrate is opposite to the second surface of the substrate.

9. The humidity sensor according to claim 8, wherein the terminal part is electrically coupled to the at least two electrodes by a through-hole provided on the substrate.

10. The humidity sensor according to claim 8, wherein the terminal part is electrically coupled to the at least two electrodes by a side surface of the substrate.

11. The humidity sensor according to claim 1, wherein the substrate is made of alumina.

12. The humidity sensor according to claim 1, wherein the substrate is made of glass.

13. The humidity sensor according to claim 1, wherein the substrate is made of silicon.

14. The humidity sensor according to claim 13, further comprising an insulating film formed on the substrate.

15. The humidity sensor according to claim 1, wherein the fluorine polymer film is formed by coating the humidity sensing film with a solution containing a fluorine polymer and subsequently heat treating the humidity sensing film.

16. A method for producing a humidity sensor, comprising the steps of:
    attaching at least two electrodes to a first surface of a substrate;
    coating the at least two electrodes and the first surface of the substrate to form a humidity sensing film comprised of an alkali metal compound and a metal oxide selected from the group consisting of manganese oxide, lead oxide and mixtures thereof;
    coating the humidity sensing film with a fluorine polymer film;
    forming a terminal part on a second surface of the substrate; and
    electrically coupling the terminal part to one of the at least two electrodes.

17. The method of claim 16, wherein the humidity sensing film is formed by coating and heating a solution containing manganese ion, lead ion and an alkali metal ion.

18. The method of claim 16, wherein the humidity sensing film is formed by coating and heating a solution containing manganese ion and an alkali metal ion.

19. The method of claim 16, wherein the humidity sensing film is formed by coating and heating a solution containing lead ion and an alkali metal ion.

20. The method of claim 16, wherein the humidity sensing film is coated on the first surface of the substrate by spin coating.

21. The method of claim 16, wherein the humidity sensing film is coated on the first surface of the substrate by screen printing.

22. The method of claim 16, wherein the at least two electrodes are circular interdigital electrodes.

* * * * *